United States Patent [19]

Hildenbrand et al.

[11] Patent Number: 4,824,640
[45] Date of Patent: Apr. 25, 1989

[54] TRANSPARENT TEST STRIP SYSTEM

[75] Inventors: Karlheinz Hildenbrand, Krefeld; Hans-Hagen Von Döhren, Bochum-Langendreer; Hermann Perrey, Krefeld; Klaus Wehling, Wuppertal, all of Fed. Rep. of Germany

[73] Assignee: Bayer Aktiengesellschaft, Leverkusen, Fed. Rep. of Germany

[21] Appl. No.: 923,536

[22] Filed: Oct. 27, 1986

[30] Foreign Application Priority Data

Nov. 15, 1985 [DE] Fed. Rep. of Germany ....... 3540526

[51] Int. Cl.$^4$ .............................................. G01N 31/22
[52] U.S. Cl. ........................................ 422/56; 422/57; 422/58; 427/2; 436/165; 436/170
[58] Field of Search ........................... 422/56, 57, 58; 436/170, 165; 435/805; 427/2

[56] References Cited

U.S. PATENT DOCUMENTS

| | | | |
|---|---|---|---|
| 4,144,306 | 3/1979 | Figueras | 422/56 |
| 4,258,001 | 3/1981 | Pierce et al. | 422/56 |
| 4,275,031 | 6/1981 | Fischer et al. | 422/58 X |
| 4,486,537 | 12/1984 | Koyama et al. | 422/56 X |
| 4,582,684 | 4/1986 | Vogel et al. | 422/57 |

Primary Examiner—Barry S. Richman
Assistant Examiner—Jill Johnston
Attorney, Agent, or Firm—Sprung Horn Kramer & Woods

[57] ABSTRACT

A transparent reagent carrier layers in analytical agents for dry chemical detection of constituents of aqueous sample solutions, the reagent carrier layer consisting of a water-soluble or water-swellable component and a film-forming component.

11 Claims, No Drawings

TRANSPARENT TEST STRIP SYSTEM

BACKGROUND OF THE INVENTION

1. Field of the Invention

The present invention relates to a transparent test strip system for determination by transmission photometry of one component of a liquid, in particular, a body fluid.

2. Background Information

The determination of one component in a liquid sample with the aid of test strips belongs to the established methods of diagnostic chemistry. In comparison with conventional wet chemical methods, such analyses are quicker and easier to carry out. In contrast, the accuracies customary in wet chemistry have as a rule not yet been reached with test strips. Many attempts have therefore been made to overcome these disadvantages (European Patent No. 0,064,710, DOS (German Published Specification) No. 3,130,749, DOS (German Published Specification) No. 2,332,760, DOS (German Published Specification) No. 2,532,918, DOS (German Published Specification) No. 2,602,975 and DOS (German Published Specification) No. 3,016,618). The structure of the carrier matrix and the evaluation method, in particular, play an important role in the context of these developments. The replacement of paper by synthetic polymers as the carrier material produced good progress here. With a suitable structural buildup, such systems are also suitable directly for application of whole blood. In the polymeric test strip systems for whole blood analysis known hitherto, the red blood cells are removed via microporous structural elements. On the other hand, the serum can penetrate into the reaction space of the matrix, where a specific color reaction occurs which, for example, can be evaluated after the red blood cells have been wiped off.

The structural build-up of such test elements, however, is as a rule relatively complicated, which also makes reproducible production difficult.

In addition to visual comparison, determination methods by reflectance photometry, in particular, have gained acceptance for evaluating the test strip reactions. However, such reflectometric determinations are based on physical approximation methods (Kubelka-Munk theory) and do not offer the precision of the transmission determination used in wet chemistry (Lambert-Beer Law).

SUMMARY OF THE INVENTION

The present invention relates to a transparent diagnostic agent which is distinguished by a simple structural build-up and simple production and permits evaluation by transmission photometry.

The invention particularly relates to transparent reagent carrier layers in analytical agents for dry chemical detection of constituents of aqueous sample solutions, the reagent carrier layer consisting of a water-soluble or water-swellable component and an essentially water-insoluble, film-forming component.

It was known that water-resistant absorbent test-strip matrices can be prepared from aqueous dispersions in the presence of insoluble film openers (DOS (German Published Specification) No. 2,910,134).

However, opaque porous films are obtained due to the filler particles included, and these are unsuitable for transmission evaluations.

It has now been found, entirely surprisingly, that transparent film systems which absorb liquid are obtained if casting solutions consisting of a mixture of a dispersion or solution of a film-forming polymer which is essentially water-insoluble and a water-swellable or water-soluble component are used to produce the films.

If such casting solutions are applied to substrates which adhere well and are then dried, pore-free films which, on the basis of their swelling capacity, absorb defined amounts of liquid are obtained. The swelling properties of the film systems can be varied via the ratio of film-forming polymer to water-swellable component. If the reagents required for a particular detection reaction are introduced into the casting solution, coating a substrate and drying gives the transparent detection elements according to the invention.

DETAILED DESCRIPTION OF THE INVENTION

The detection reagents can be incorporated in various ways, depending on the solubility of the reagents and the solvent of the polymer matrix system. If the detection reagents are soluble in the solvent system of the matrix casting solution, the procedure can accordingly be carried out in a homogeneous phase. Thus, for example, water-soluble detection reagents are incorporated into aqueous casting solutions by dissolving the reagents in water and then stirring the solution into the matrix casting solution without further auxiliaries.

If the detection reagents are insoluble in the solvent system of the casting solution, the emulsion techniques which are known per se (see, for example, "Emulsionen", Ullmann, Enzyklopadie der technischen Chemie ("Emulsions", *Ullmann, Encyclopaedia of Industrial Chemistry*), 10, 449–473, Verlag Chemie (1975)) can be used. The two most important emulsion techniques are mechanical and chemical emulsification. Mechanical emulsification can be carried out, for example, with the aid of high-speed stirrers, auxiliary solvents and emulsifiers frequently also being added. In chemical emulsification, one or more emulsifiers are employed, it being possible to obtain oil-in-water (O/W) or water-in-oil (W/O) emulsions, depending on the corresponding HLB values (Hydrophilic Lipophilic Balance). Suitable emulsifiers are likewise listed in the abovementioned literature reference. In this connection, it should be mentioned that the ionic polyurethane dispersions preferably used for the detection elements according to the invention themselves have emulsifier properties.

Suitable film-forming components of the casting solution are polymers of natural or synthetic origin which are soluble in organic solvents, such as, for example, cellulose esters, polyvinyl acetate, polyamides, polycarbonates, polyether-carbonates and mixtures or copolymers thereof. Preferred film-forming agents are aqueous polymer dispersions, for example of polyvinyl or polyacrylic compounds, vinyl copolmers, polystyrenesulphonic acids, polyamids and polyurethanes, and mixtures thereof. Polyurethane dispersions which are nonionic or, preferably, ionic are especially suitable, it being possible for the ionic radicals to be sulphonate, carboxylate or ammonium groups.

The known water-soluble or water-swellable polymers, such as, for example, polyacrylamides, polyacrylic acids, cellulose ethers, polyethyleneimine, polyvinyl alcohol, copolymers of vinyl alcohol and vinyl acetate, gelatine, agarose, alginates and polyvinylpyrolidone, which has proved particularly suitable, are possible as the second polymer component ("swelling component").

To prepare the casting solution for the transparent test strips according to the invention, the solution or dispersion of the film-forming component is mixed with the solution or dispersion of the swelling component and this mixture is applied to a carrier and dried. It is typical of the present invention that the solvent or diluent of the film-forming component and that of the swelling component are miscible with one another, and as a rule are even identical.

Thus, suitable casting solutions can be obtained from organic solvents, for example, by mixing a solution of cellulose acetate in methylene chloride/methanol (film-forming agent) and a solution of cellulose ether (soluble or swellable component) in methylene chloride/methanol with one another.

In the preferred aqueous casting solutions, aqueous polymer dispersions are mixed with an aqueous solution of the swelling component, such as, for example, polyvinyl acetate dispersions with cellulose ethers, polyurethane dispersions with polyvinyl alcohol, polyurethane dispersions with gelatine or polyurethane dispersions with polyvinylpyrrolidone, which have proved to be especially suitable. Crosslinking agents can also be added to the casting solutions, these leading to an increased resistance of the reagent carrier layers to water.

The ratio of film-forming component to swelling component is an important parameter for the required mode of functioning of the test systems according to the invention. Thus, it has not been possible to obtain suitable detection elements from casting solutions in which the swelling component was absent. Only a reaction which proceeds extremely slowly, if any, was observed. In contrast, contents of swelling component which are too high lead, after addition of the sample, to serve clouding or to detachment phenomena when the excess sample is wiped off. The weight ratio of film-forming to swelling component depends on the polymers used and on the envisaged intended use. It can be 50:1 to 1:1, preferably 10:1 to 5:1, the film-forming component being employed in excess.

Transparent films of plastic, such as, for example, of polyethylene terephthalate, are a suitable carrier material for the transparent reagent carrier layers according to the invention. If reflecting carrier films are used, the detection elements can also be evaluated by reflectometry.

The agents according to the invention are usually employed as single-layer systems. However, they can also be used as a component of a multi-layer system. The diagnostic detection agents according to the invention are described in more detail in the following non-limiting examples.

EXAMPLE 1

To detect glucose in urine or whole blood, a casting solution of the following composition was prepared: 28.9 g of anionic polyurethane dispersion (40% strength in water), 0.3 g of 3,3',5,5'-tetramethylbenzidine, dissolved in 1 ml of dimethylformamide, 10.6 g of polyvinylpyrrolidone (molecular weight 350,000), 20% strength solution in phosphate buffer of pH 5.5, 0.2 g of 5% strength ascorbic acid in water, 18 KU of glucose oxidase and 72 KU of peroxydase, in 10 ml of phosphate buffer of pH 5.5, and 0.2 g of sodium dioctylsulphosuccinate.

The anionic polyurethane dispersion is a reaction product of 82 parts of a polyester of adipic acid, hexanediol and neopentylglycol (molecular weight=1,700), 15 parts of hexamethylene diisocyanate, 2 parts of Na ethylenediamine-ethylsulphonate and 1 part of ethylenediamine.

The 3,3',5,5'-tetramethylbenzidine was incorporated into the anionic polyurethane dispersion with the aid of a high-speed stirrer, dimethylformamide being used as an auxiliary solvent.

The casting solution was coated in a layer thickness of 150 μm onto a polyethylene terephthalate film and dried with warm air. A transparent test strip system adhering to the film was thereby obtained.

Test with aqueous glucose solutions (0.1; 0.5; 1.0%):
  The glucose solutions were placed on the test strip surface and wiped off with cotton wool after 15 seconds. Transparent blue colorations which were increasingly more intense according to the increasing glucose concentration and allowed clear differentiation developed within 30 seconds.
Test with whole blood:
  One drop of blood was placed on the test strip surface and wiped off with cotton wool after a residence time of 15 seconds. A homogeneous transparent blue coloration developed.
Evaluation by transmission photometry:
  Test liquids;
  Aqueous glucose solutions with different glucose concentrations (0, 50, 100, 200, 300, 500, 800, 1,000 mg/dl).

Increasing extinction values were measured according to the increasing glucose concentrations, and showed a linear dependence in the range from 0 to 800 mg/dl. The wavelength of the measurement radiation was 640 nm.

Further casting solutions from which suitable transparent glucose test strips were prepared are described in the following examples. The incorporation of the reagent, production of the film and testing were carried out as in Example 1.

EXAMPLE 2

Film-forming component:
100 g of aqueous polyvinyl acetate dispersion (Vinnapas M 50 ®, Wacker)
Swelling component:
37.7 g of polyvinylpyrrolidone solution (20 percent strength in phosphate buffer (pH 5.5).

EXAMPLE 3

Film-forming component:
100 g of aqueous butadiene/acrylonitrile copolymer dispersion (Perbunan-Latex ®, Bayer AG) and
Swelling component:
35.7 g of polyvinylpyrrolidone solution (20 percent strength in phosphate buffer of pH 5.5).

EXAMPLE 4

Film-forming component:
25 g of anionic polyurethane dispersion (see Example 1)
Swelling component:
90 g of hydroxyethyl-cellulose solution (2 percent strength in water, Tylose H 300, Hoechst (AG).

EXAMPLE 5

Film-forming component:

50 g of cellulose acetate solution (20 percent strength in methylene chloride/methanol 4:1, Cellit T 700, Bayer AG)

Swelling component:

100 g of methylcellulose solution (2 percent strength in methylene chloride/methanol 4:1, Walocel MT 10,000 GO, Wolff-Walsrode AG).

EXAMPLE 6

Two-layered, transparent glucose detection system (a) Casting solution for the chromogen Layer: 10 g of anionic polyurethane dispersion (see Example 1), 0.08 g of 3,3',5,5'-tetramethylbenzidine, 0.7 ml of ascorbic acid (20 percent strength in $H_2O$), 0.43 g of polyvinylpyrrolidone solution (20 percent strength in phosphate buffer of pH 5.5) and 0.04 g of Na dioctylsulphosuccinate.

(b) Casting solution for the enzyme layer: 10 g of anionic polyurethane dispersion (see Example 1), 0.43 g of polyvinylpyrrolidone solution (20 percent strength in phosphate buffer of pH 5.5), 0.35 ml of glucose oxidase solution (1374 units/ml), 8.0 mg of peroxidase (60 units/mg) and 0.04 g of Na dioctylsulphosuccinate.

Casting solutions (a) and (b) were coated and dried in succession on polyethylene terephthalate film. In the test with aqueous glucose solutions, concentration-dependent blue colorations were observed analogously to those in Example 1.

It will be appreciated that the instant specification and claims are set forth by way of illustration and not limitation, and that various modifications and changes may be made without departing from the spirit and scope of the present invention.

What is claimed is:

1. A transparent reagent carrier layer for an analytical agent for dry chemical detection of constituents of aqueous sample solutions, comprising within one layer a water-soluble or water-swellable component selected from the group consisting of a polyacrylamide, a polyacrylic acid, cellulose ether, polyethyleneimine, polyvinyl alcohol, a copolymer of vinyl alcohol and vinyl acetate, gelatine, agarose, alginate and polyvinyl pyrrolidone, and an essentially water-insoluble film-forming component selected from the group consisting of a polystyrenesulfonic acid, a cellulose ester, a polyvinyl acetate, a polyamide, a polycarbonate, a polyether-carbonate, a ionic polyurethane, a non-ionic polyurethane, mixtures thereof and copolymers thereof.

2. A reagent carrier layer according to claim 1, wherein the film-forming component is an ionic polyurethane having one or more ionic radicals selected from the group consisting of a sulphonate group, a carboxylate group and an ammonium group.

3. A reagent carrier layer according to claim 1, wherein the weight of the film-forming component to the water-soluble or water-swellable component is the range from 50:1 down to 1:1.

4. A reagent carrier layer according to claim 3, wherein the weight ratio is in the range from 10:1 down to 5:1.

5. A process for the preparation of a reagent carrier layer according to claim 1, the process comprising mixing a solution or dispersion of one or more of the film-forming components and a solution or dispersion of one or more of the water-soluble or water-swellable components, applying the resultant mixture to a carrier and drying said mixture on said carrier.

6. A process according to claim 5, wherein the solvents or diluents used for the preparation of the solutions or dispersions of the film-forming component and the water-soluble or water-swellable component are miscible with one another.

7. A process according to claim 5, wherein the same solvent or diluent used for the preparation of the solution or dispersion of the water-soluble or water-swellable component is used to prepare the solution or dispersion of the film-forming component.

8. A process according to claim 5, wherein the carrier is polyethylene terephthalate.

9. An analytical agent for dry chemical detection of constituents of an aqueous sample solution comprising a reagent carrier according to claim 1 and one or more detection reagents for determination of the constituents to be detected.

10. A method for the dry chemical detection of constituents of an aqueous sample solution comprising bringing the sample solution into contact with an analytical agent according to claim 9 and monitoring resultant detection reaction.

11. A method according to claim 10, wherein the detection reaction is monitored by transmission photometry.

* * * * *